US006887247B1

(12) United States Patent
Couture et al.

(10) Patent No.: US 6,887,247 B1
(45) Date of Patent: May 3, 2005

(54) CAS DRILL GUIDE AND DRILL TRACKING SYSTEM

(75) Inventors: Pierre Couture, Montréal (CA); Dominic Picard, Verdun (CA); Louis-Philippe Amiot, Montréal (CA)

(73) Assignee: Orthosoft Inc., Montreal (CA)

( * ) Notice: Subject to any disclaimer, the term of this patent is extended or adjusted under 35 U.S.C. 154(b) by 179 days.

(21) Appl. No.: 10/123,237

(22) Filed: Apr. 17, 2002

(51) Int. Cl.⁷ .............................................. A61B 17/58
(52) U.S. Cl. ..................................... 606/96; 408/72 R
(58) Field of Search ........................ 408/72 R; 606/96

(56) References Cited

U.S. PATENT DOCUMENTS

| | | | |
|---|---|---|---|
| 5,895,389 A | 4/1999 | Schenk et al. | |
| 6,120,511 A | 9/2000 | Chan | |
| 6,205,411 B1 | 3/2001 | DiGioia, III et al. | |
| 6,236,875 B1 | 5/2001 | Bucholz et al. | |
| 6,478,802 B2 * | 11/2002 | Kienzle et al. | 606/130 |
| 2002/0016599 A1 | 2/2002 | Lea et al. | |

FOREIGN PATENT DOCUMENTS

| | | |
|---|---|---|
| DE | 100 05 880 | 8/2001 |
| WO | WO 9929253 | 6/1999 |

* cited by examiner

*Primary Examiner*—Cary E. O'Connor
*Assistant Examiner*—Candice C. Stokes
(74) *Attorney, Agent, or Firm*—Ogilvy Renault (57) ABSTRACT

A drill guide assembly for a drilling tool having a chuck engaging a bit portion comprising a tip and a length extending from the chuck, the drill guide assembly comprising a first member, a second member and a trackable member. The first member is adapted to abut a workpiece surface and defines a central aperture therethrough adapted to receive the bit portion of the drilling tool. The second member is adapted to be axially displaced with respect to the first member and is axially biased therefrom, and defines a central aperture therethrough adapted to receive the bit portion of the drilling tool. The trackable member, fastened to the second member, comprises a detectable element adapted to be located and tracked in three dimensional space, thereby defining the position and movement of the second member and therefore that of the bit portion of the drilling tool.

27 Claims, 7 Drawing Sheets

CAS DRILL GUIDE AND DRILL TRACKING SYSTEM

TECHNICAL FIELD

The present invention relates to surgical devices, and more particularly to a drill guide adapted to provide guidance and tracking of a drilling tool when used in conjunction with a computer aided surgical system.

BACKGROUND OF THE INVENTION

Many surgical procedures, particularly those used in orthopaedic surgery, require holes to be drilled in a bone of a patient. Surgical drills have long been used for this purpose, and various mechanical guidance instruments exist to enable a surgeon to accurately drill a hole to a correct depth and without danger of damaging the surrounding tissue. Such drill guides often provide a visual depth gauge which requires the surgeon to read the depth of the drilled hole off a graduated scale-on the instrument.

U.S. Pat. No. 5,895,389 issued Apr. 20, 1999 to Schenk et al. discloses such a drilling guide and measuring instrument. The guide generally comprises a sleeve and a plunger that telescopes within the sleeve, both having axial bores adapted to receive and guide a portion of a drilling tool that protrudes beyond a drill chuck. A plurality of fingers on the forward end of the plunger are biased inwardly by an inside wall of the sleeve, providing a frictional, sliding fit. Therefore the plunger and sleeve retain their relative telescopic position after they have been partially collapsed. Gradations on the side of the plunger indicate the relative movement of the plunger with respect to the sleeve, and therefore the penetration depth of the drill. The sleeve preferably has a small handle for controlling the drilling guide. An alignment bore extends through the handle in parallel with the central axis of the sleeve and plunger bores. By sliding the handle with the alignment bore over a guide wire pre-inserted into the workpiece, the drilling guide may be aligned with the parallel wire at a predetermined distance therefrom.

With the advent and growing use of computer aided surgery (CAS), much greater accuracy is possible for many surgical procedures. Surgeons can now plot on a computer generated 3D model of the patient, before the actual procedure, the ideal location, orientation and depth of a drill hole, for example. During the surgery, position of the instruments with respect to scanned images of the body parts can be displayed on monitors to guide the surgeon during the procedure.

One CAS system currently employed comprises the use of at least two cameras, located at different stationary reference points, which simultaneously record the location of a moving three point axis. Knowing the positions of the reference points, the unique position in space of the three point axis, and therefore any object to which the axis is fixed, is uniquely defined and can therefore be precisely tracked.

While such instrumentation tracking systems work well for some applications, problems nevertheless exist with certain current surgical uses of visually tracked systems. In order for the cameras to record accurate simultaneous images of the three point tracker axis, and for the location of the points of the axis to be correspondingly precisely computed, the visual images of the axis must remain relatively distortion free. As such, any displacement of the tracker axis with respect to the surgical tool to which it is fastened, results in inaccurate calculation of the exact three dimensional (3D) spatial position, and therefore inaccurate representation on the computer monitors of the operative instrument with respect to the patient. Therefore, the attachment brackets and fixation adapters for securely locating the tracker axis to the tool are often complex.

CAS systems have been employed in conjunction with a surgical drill to attempt to monitor the location and depth of holes drilled into the bone of a patient for such surgical procedures as pin implantation and prosthesis fixation. For such applications, CAS three point tracker axis have been fastened directly to the drill.

A major problem associated with current attachment methods for fixing a CAS tracker axis to a drilling tool, is that many hospitals use significantly different drill systems. Therefore fastening a CAS tracker axis to each type of drill requires many parts and a completely different set of complex fixation adapters in every case. This necessitates a custom installation for fixing a CAS tracker axis to each and every type of surgical drill, thereby adding considerable expense to CAS systems which already represent a significant expenditure for hospitals. Additionally, the added bracketry required to sufficiently fix the CAS tracker axis to the drill, causes an unnecessary reduction in the freedom of movement that the surgeon has to manipulate the drill.

Therefore, accurate real time visual or electromagnetic tracking of instruments used to drill holes during surgeries has been so far been impractical and expensive for widespread use with all types of surgical drilling systems.

SUMMARY OF THE INVENTION

A need exists to provide an improved universal drilling instrument for use with all types of surgical drill systems such that a CAS system can produce an accurate visual representation of the drill bit with respect to the workpiece, and therefore ensures the surgeon can accurately determine the hole location, depth and orientation created using any type of drilling tool system.

It is an object of the present invention to provide a universal instrument which allows CAS drill tracking.

It is another object of the present invention to provide an improved surgical drill guide.

It is a further object of the present invention to provide a surgical drill guide that includes a CAS tracking axis.

It is a further object of the present invention to provide a CAS tracked surgical drill guide that is easy to use.

It is a further object of the present invention to provide a surgical drill guide capable of providing improved drilling accuracy.

It is a further object of the present invention to provide a surgical drill guide capable of providing improved drilling precision.

It is a further object of the present invention to provide a surgical drill guide able to precisely indicate hole depth.

Therefore, in accordance with the present invention, there is provided a drill guide assembly for a drilling tool having a chuck engaging a bit portion comprising a tip and a length extending from the chuck, said drill guide assembly comprising: a first member adapted to abut a workpiece surface and defining a central aperture therethrough adapted to receive the bit portion of the drilling tool; a second member adapted be axially displaced with respect to said first member and being axially biased therefrom, and defining a central aperture therethrough adapted to receive the bit portion of the drilling tool; and a trackable member, fastened to said second member and comprising a detectable element adapted to be located and tracked in three dimensional space, thereby defining position and movement of said second member and therefore that of the bit portion of the drilling tool.

In accordance with the present invention there is also provided a drilling system comprising a drill and a drill guide assembly, the drill having a chuck engaging a bit portion having a tip and extending from the chuck a predetermined length, said drill guide assembly comprising: a guide member defining a central aperture therethrough adapted to receive the bit portion of the drilling tool; a collar member defining a central aperture therethrough dimensioned to intimately receive said guide member; said collar member and said guide member being axially biased, and adapted to telescope with respect to one another; one of said guide member and said collar member being adapted to abut a workpiece surface, the other of said guide member and said collar member being adapted to be axially displaced with respect to said one of said guide member and said collar member; and a trackable member, fastened to said other of said guide member and said collar member, having detectable element adapted to be located and tracked in three dimensional space, said detectable element defining the position and movement of said other of said guide member and said collar member, and therefore defining the position and movement of the bit portion of the drilling tool.

There is additionally provided, in accordance with the present invention, a method for defining the position and movement of a drill having a bit portion engaged in a chuck, said method comprising: providing a drill guide adapted to receive the bit portion of the drill; fixing a trackable member comprising detectable element to a mobile portion of said drill guide, said detectable element defining a unique position and orientation in three dimensional space of said trackable member and therefore said drill guide; inserting the bit portion of the drill into said drill guide; positioning the bit portion over a workpiece surface and engaging said workpiece surface with a proximal end of one of the bit portion and said drill guide; and locating a position and tracking movement of said trackable member fixed to said drill guide, and thereby locating the position and tracking the movement of the bit portion.

BRIEF DESCRIPTION OF THE DRAWINGS

Further features and advantages of the present invention will become apparent from the following detailed description, taken in combination with the appended drawings, in which:

FIG. 1b is a longitudinal sectional view taken along line 1b—1b of the CAS drill guide assembly of FIG. 1a.

FIG. 3b is an end view of the collar member shown in FIG. 3a.

FIG. 3c is a longitudinal sectional view of the collar member shown in FIG. 3a.

FIG. 4b is an end elevation view of the guide member shown in FIG. 4a.

FIG. 5b is a front elevation view of the CAS trackable member shown in FIG. 5a.

DETAILED DESCRIPTION OF THE PREFERRED EMBODIMENT

The computer aided surgery (CAS) drill guide assembly 10 generally comprises a collar member 12, a guide member 14, and a trackable member 16. The guide member 14 is adapted to telescope longitudinally within the sleeve collar member 12.

Figure 1A:
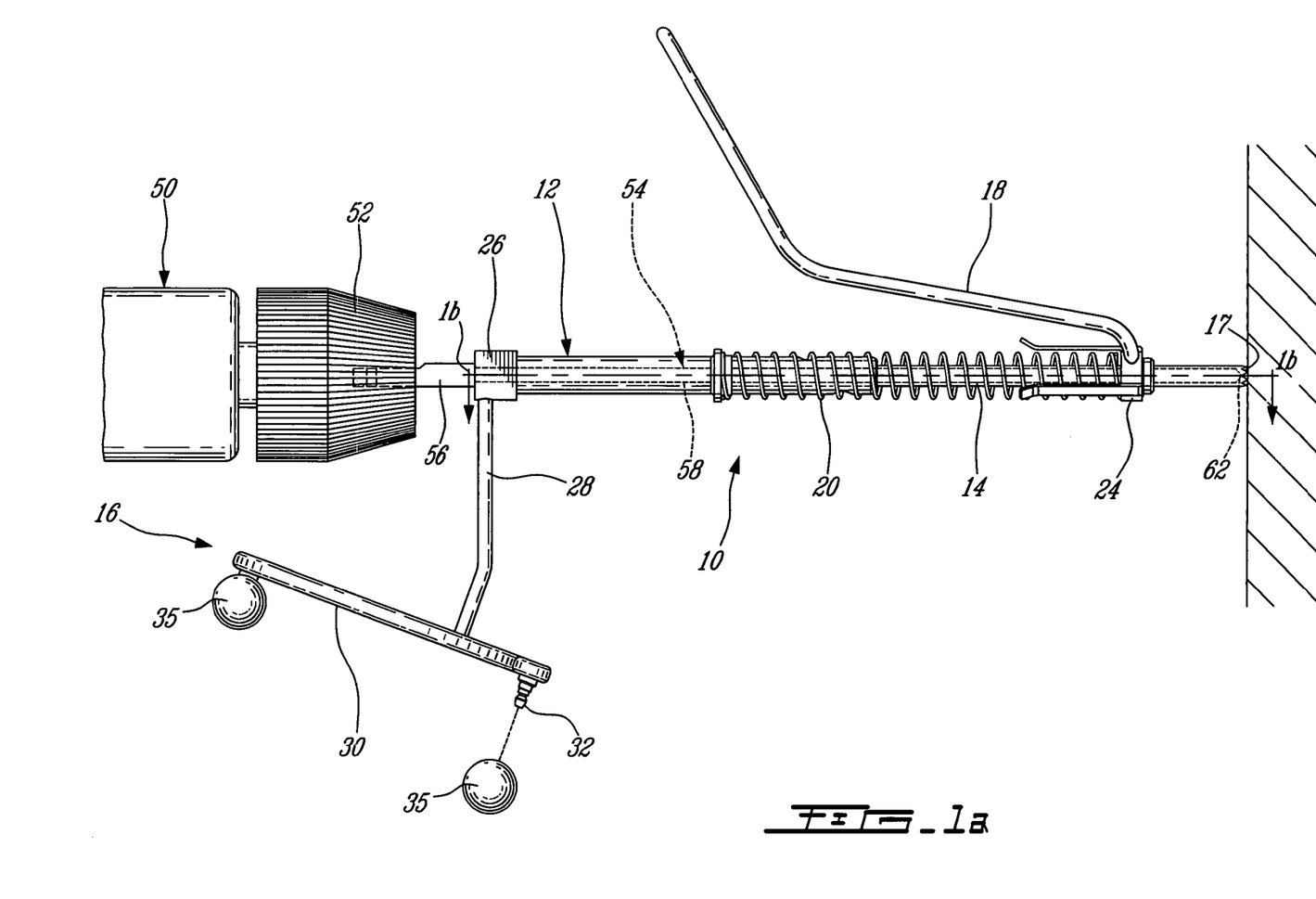
FIG. 1a is a top view of the CAS drill guide assembly of the present invention.
Figure 1B:
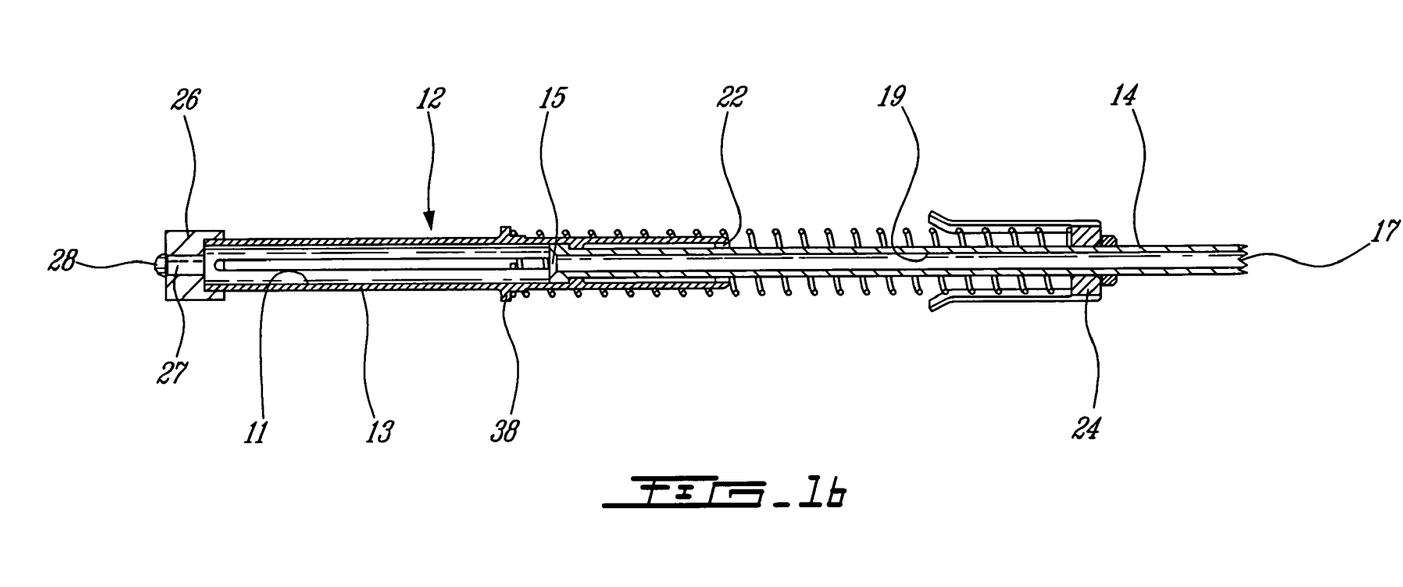
Figure 2:
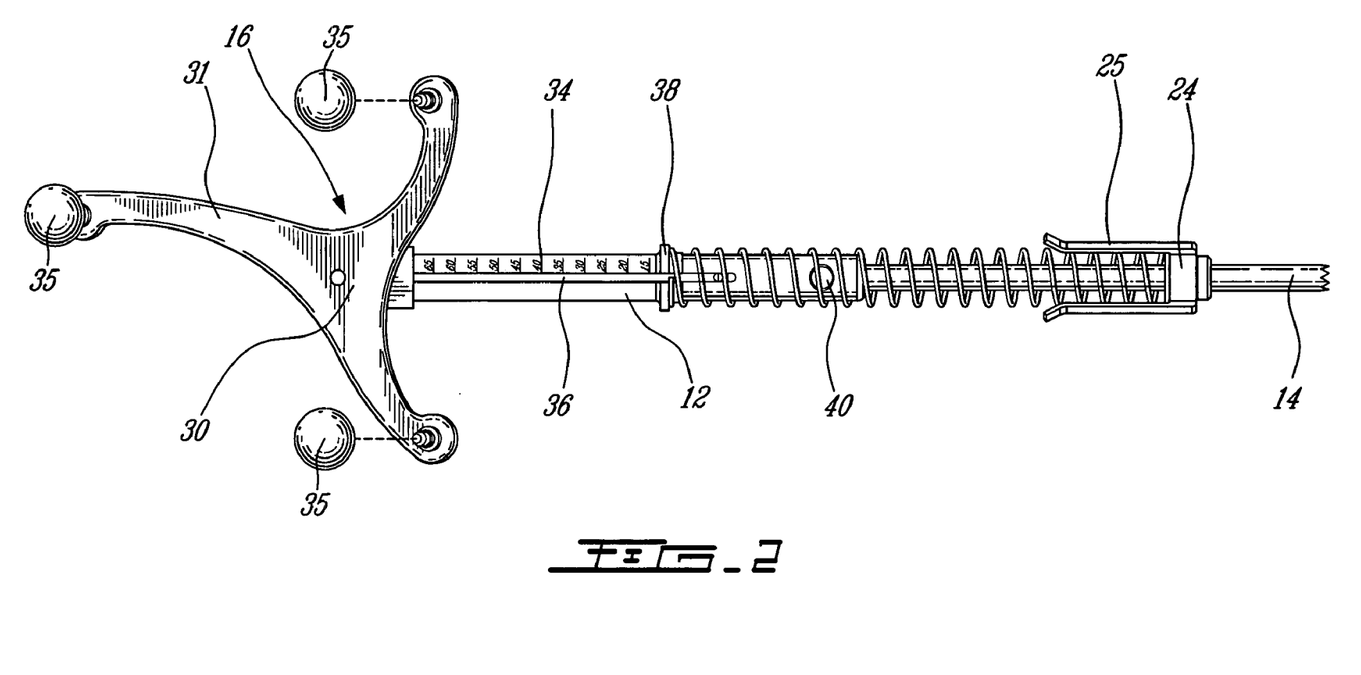
FIG. 2 is a perspective side view of the CAS drill guide assembly of the present invention.
Figure 4A:
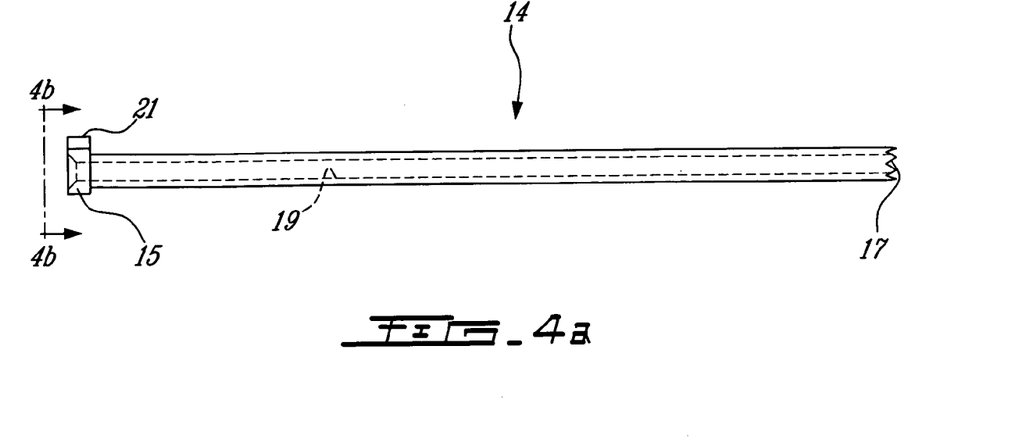
FIG. 4a is a side elevation view of the guide member of the drill guide of the present invention.
Figure 4B:
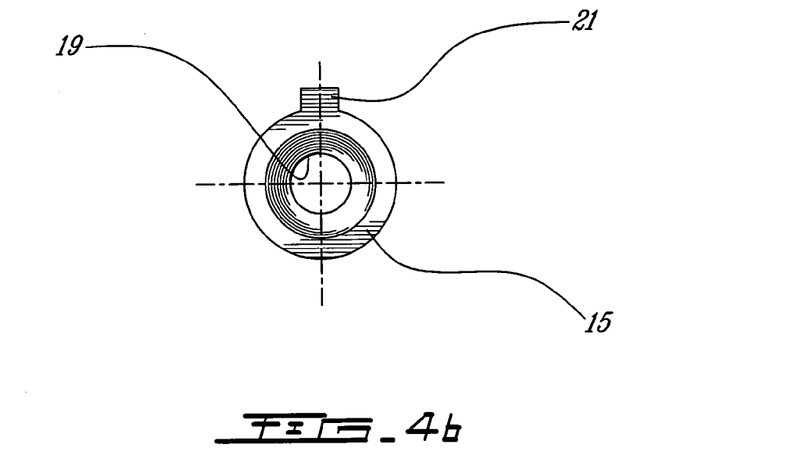
Figure 4C:
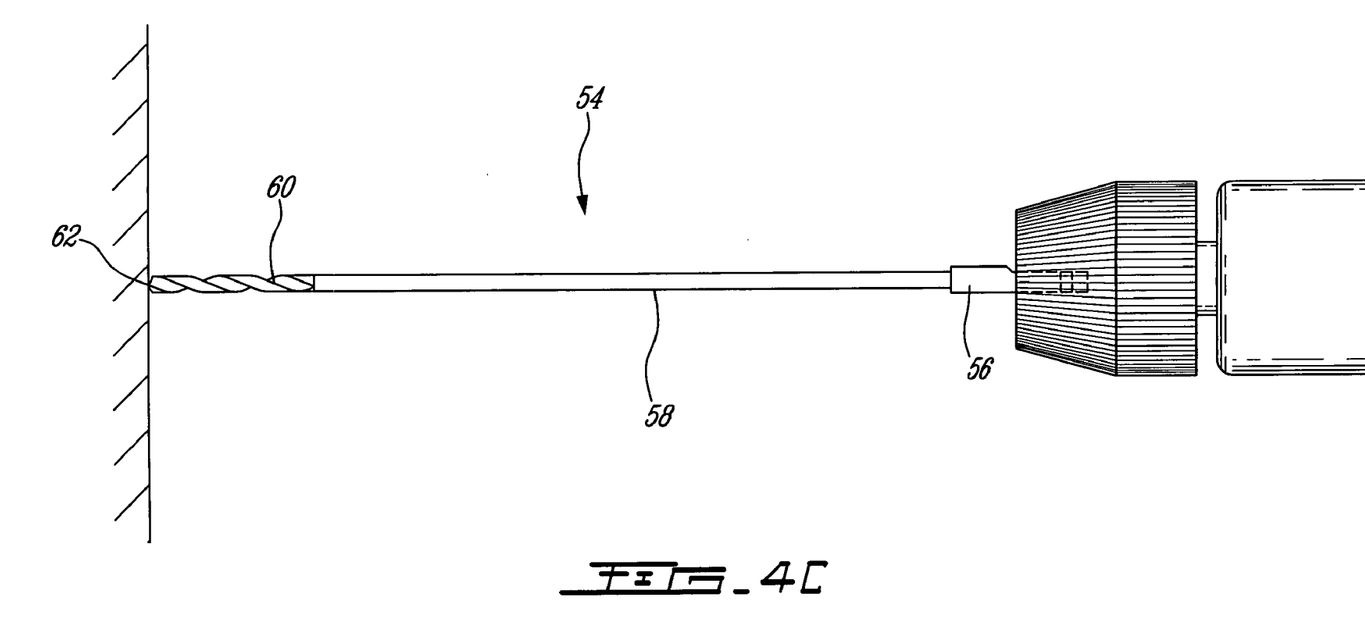
FIG. 4c is a side elevation view of the drill bit of the drilling tool to be used with the drill guide of the present invention.

Referring generally to the assembly shown in FIGS. 1a, 1b and 2, the guide member 14 abuts the workpiece at a proximal end having teeth 17 adapted to frictionally engaged the bone of the patient or other workpiece surface. A chuck portion 52 of a drilling tool 50 retains a drill bit 54 having a distal protrusion 56 which abuts end cap 26 of the collar member 12. Spring 20 generally provides resistance, such that collar member 12 is biased from the guide member 14. The collar member 12 generally defines an inner bore 11, and comprises an outer cylindrical surface 13. A circular flange 38 radially projecting from the outer surface 13 of the collar member 12, provides a reaction point for the spring 20. The end cap 26 fits over the open end of the collar member 12 and defines a central circular aperture 27 therein for receiving the drill bit 54. The shaft 58 of the drill bit 54 shown in further detail in FIG. 4c, is adapted to extend through the inner bores in both the collar member 12 and the guide member 14, such that the tip 62 of the drill bit's cutting front 60 is preferably near the proximal end 17 of the guide member 14.

The CAS drill guide of the present invention is preferably intended to be used in conjunction with an optical tracking system which uses a network of cameras to locate the markers 32, so that their position and movement can be tracked during the surgery. Pre-operative computed tomography (CT) scans of the patient create a three dimensional anatomical model which is displayed on monitors during surgery and provides the surgeon with an accurate representation of the specific body parts or targeted elements of the patient. Scanned images from a magnetic resonance imaging (MRI) system can also be used to create the 3-D virtual models of the patient. At the beginning of the surgery, an anatomical registration is performed which matches the patient anatomy with the 3-D digitized model displayed on the monitor, such that the position of the tool can be shown graphically in real time with respect to the displayed model of the patient.

The length of the drill bit is preferably chosen such that when the drill chuck is pressed against the end cap 26 of the drill guide, the drill bit extends therethrough such that it just reaches the workpiece surface. A shorter drill bit can be also accommodated, however determination of the zero point, or the tracker position when the tip of the drill bit just touches the workpiece surface, must be known to accurately determine the depth of the subsequently drilled hole. By rapidly moving the mobile portion of the drill guide, onto which the trackable member is engaged, toward the workpiece, the zero point is found when the tip of the bit portion of the drill makes contact with the workpiece surface. The position of the trackable member, which will be described in further detail below, when it comes to a sudden stop defines the zero position. Therefore, the CAS system can use this point as a reference from which to calculate hole depth, whereby any further movement of the drill towards the workpiece surface will be registered by the CAS system as creating a hole in the workpiece. This also enables the drill bit tip position to be registered by the CAS system, such that the drill bit can be displayed on the CAS monitors in relation to the three-dimensional digitized model of the patient's bone. The length of the drill bit used could also be pre-selected by the surgeon or CAS system operator from among a list of drill bit types in the CAS software, such that once the drill guide is registered, the position of the drill bit tip with respect to the drill guide is known and can be displayed on the CAS monitors in relation to the bone model.

The depth of hole drilled into the workpiece is calculated by the CAS system, and can be visually displayed on CAS system monitors. This provides the surgeon with a precise, real time indication of the hole depth. This CAS calculated depth can be cross-checked with the physical visual depth sight on the drill guide, as described below, to ensure that the hole depth is accurately displayed on the monitor. The CAS system first prompts for a hole insertion point location to be selected on the outer surface of the digitized 3-D model, using a mouse, foot pedal, or other similar selection device. The distance measured between the tip of the drill bit and the chosen insertion point, can then be calculated, and indicates the depth into the workpiece that the drill bit tip has travelled.

The hole depth calculated by the CAS system can also be used by the CAS software to help select the appropriate sized screw to be used. The hole depth calculation algorithm can be linked to a database of screws or other fixations for the implant system to be used, such that the most appropriate type and size of screw can be selected and recommended to the surgeon, based on the size and depth of hole created. The recommended screw can be displayed as a 3-D visual representation or in text format indicating the most probable screw length.

Figure 3A:
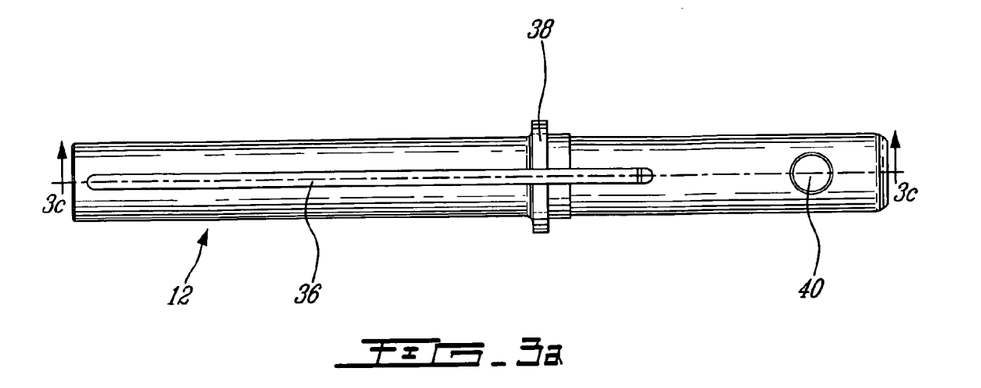
FIG. 3a is a side elevation view of the collar member of the CAS drill guide.
Figure 3B:
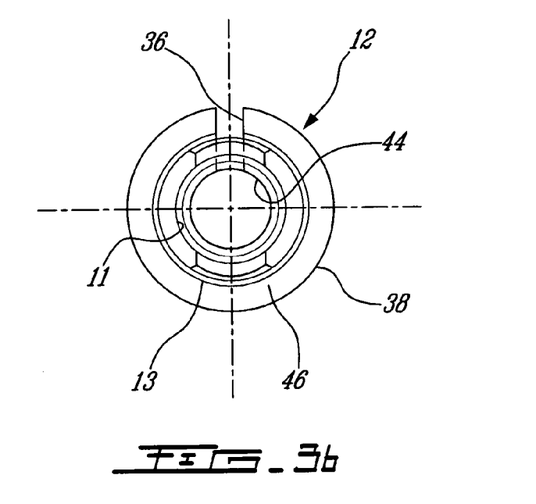
Figure 3C:
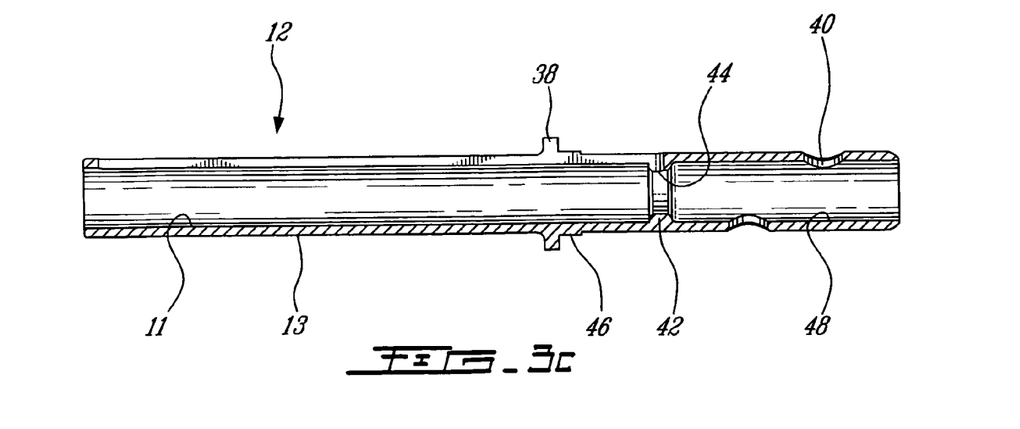

A slot 36 in the collar member provides a visual depth sight, such that when the collar member slides over the guide member, telescopically or otherwise, the position of a distal end of the guide member 14 can be seen through the sight gauge slot 36. Therefore the depth of the hole created by the drill bit in the workpiece, which directly corresponds to the distance travelled by the collar on the guide when using a drill bit of the preferable length as described above, can be read directly from the gradations 34 on the exterior surface 13 of the collar member 12. This gives the surgeon a visual verification of hole depth, and can be also used to double check or calibrate the monitor displayed CAS calculated results.

Two opposing but offset holes 40 perforate a side wall of the collar member 12 near the proximal end. These serve as cleaning holes, and permit water or other cleaning fluid to be injected inside the collar to ensure that any debris can be easily washed out. This inhibits possible build-ups of debris which might prevent the collar member from smoothly sliding on the guide member.

Figure 5A:
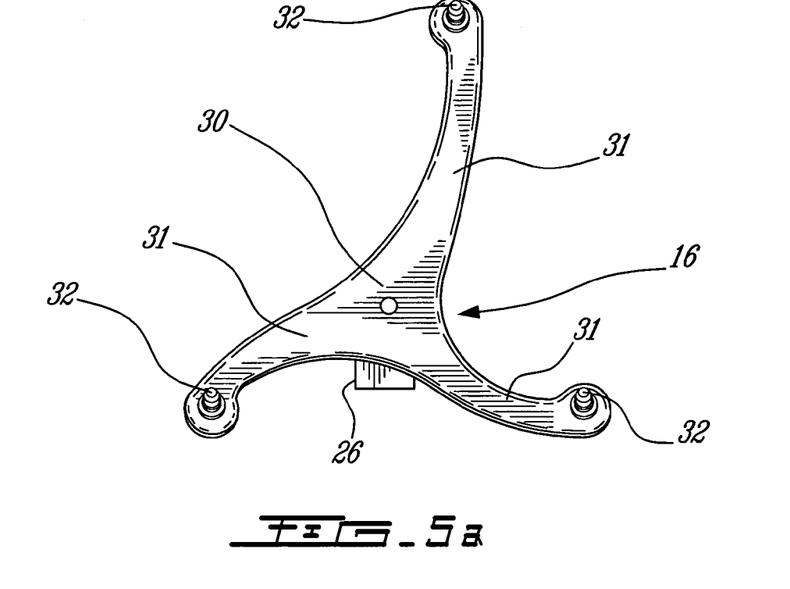
FIG. 5a is a side elevation view of the CAS trackable member of the drill guide.
Figure 5B:
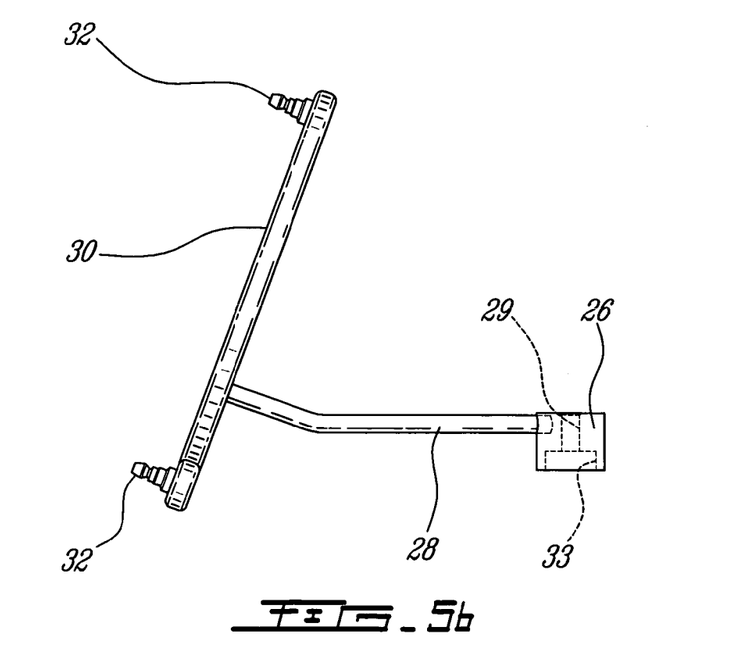

The trackable member 16 generally comprises a support rod 28, and a tracker head 30 having arm portions 31 extending generally radially and which include detectable element mounting posts 32 at the end of each arm 31. To each mounting post 32 is removably fixed an optically detectable sphere 35. The detectable spheres are coated with a retro-reflective layer in order to be detected by, for example, an infrared sensor using axial illumination. Cameras of the CAS system can therefore detect the position of each optically detectable sphere 35 illuminated by infrared. Each detectable element 35 can equally be any other type of position indicator such as a light emitting diode or detectable electromagnetic indicator, provided each can be detected by the type of sensor used by the CAS system.

The support rod 28 is fixed to the collar member 12 at the end cap 26, such that all movements of the collar member, and therefore the drill and drill bit, are duplicated by the trackable member 16.

The drill guide member 14 has a circumferential radially extending end flange 15 adapted to be intimately received in the inner bore 11 of the collar member 12. The end flange 15 of the guide member abuts the interior stop 42, located within the collar member 12, when the spring is fully extended. The guide member has a central bore 19 dimensioned to receive the drill bit of the drilling tool. A clamp 24, providing a second reaction point for the spring 20, is fastened to the exterior surface of the guide member 14 near the proximal end, at a point which provides a sufficient pre-load force on the spring. The clamp comprises an external, axially projecting, member 25. This provides an attachment point for a CAS instrument calibration tool, if required by the CAS system used.

A generally radially extending handle member 18 is fixed to the clamp 24 to provide the surgeon with greater control over the orientation of the drill guide. The added leverage possible by the handle 18, allows for significantly improved drill guide assembly control. The handle member 18 can be selectively positioned about the collar member 12, by rotating the clamp 24 to which the handle is fixed. The surgeon can therefore easily rotate the handle about the drill guide in order to find a comfortable position drilling while maintaining optimal visual contact between the tracker markers of the trackable member and the position locating cameras used to defined the position of the drill guide.

In an alternative embodiment, the trackable member can be selectively positioned about the collar member 12, by rotating the end cap 26 to which the support rod 28 of the trackable member is fixed. A ratchet type mechanism in the end cap could provide fixed rotations of trackable member, so that the surgeon can easily rotate the trackable member about the axis drill guide in order to maintain optimal visual contact between the tracker markers.

Radially extending guide tab 21 protrudes from the end flange 15 of the guide member 14. The tab 21 provides both a sight gauge marker within the depth sight slot 36 of the collar member 12, and additionally provides anti-rotation protection for the guide member within collar member. The interior bore 44 defined by the radially inwardly projecting stop 42 is adapted to intimately receive the guide member such that the collar member 12 can axially translate on the exterior surface of the guide member 14 with substantially concentric displacement. To ensure this, a metal bushing 22 is additionally located within the collar member 12 at the proximal end.

The first member abutting the workpiece and the second member abutting the drill bit in the drill chuck, depicted in the exemplary embodiment as the guide member 14 and the collar member 12 respectively, are preferably generally elongated in shape and telescope within one another. However, the first and second members can be of any other shape, subject only to practicality and ease of use by the surgeon, and are required only to move relative to one another along a path substantially similar to that of the drill bit. The two members do not have to be engaged with each other, and could therefore be separated by a third intermediate member, providing relative motion exists between the workpiece abutting member and the drill chuck abutting member.

In the preferred embodiment, the coiled compression spring 20 is located on the exterior of the drill guide assembly 10, and the member that abuts the workpiece is the guide portion of the telescoping assembly while the drill chuck abutment member is the outer collar member, it is however to be understood that the present invention would be equally functional with the collar member and guide member reversed or with the spring located within the assembly. Having the spring located on the exterior of the assembly, however, enables simplified cleaning. As such, the probability of bone debris or other material impeding compression of the spring, and therefore translation of the collar member on the guide member, is minimal. This ensures smooth drill bit motion within the workpiece. Additionally, the spring can be equivalently replaced by any other extendingly biased member, such as a sprung scissor-type mechanism.

A percentage of the helical spring is always required to remain uncompressed. By locating the spring externally, the distal spring reaction point flange 38 can be positioned at any point on the collar member. This therefore permits the minimum uncompressed length of the spring to be taken up on the collar, rather than requiring the overall tool length to be extended by this amount if the spring was to be located internally. Therefore, the exterior location of the spring additionally permits a shorter overall tool length, consequently improving the facility of use by the surgeon.

Having an axially biased assembly according to the present invention, represents a considerably advantage over drill guide assemblies having members that are radially, or frictionally, biased with one another. In such an assembly, the chuck abutting member does not automatically return to its fully extended position, but remains in the most compressed position. While this permits the hole depth sight to be read after drilling the hole, it makes drilling a plurality of hole in quick succession impractical and more time consuming. The axially biased spring system of the present invention, returns the drill guide to its fully extended resting position after each hole drilled, and therefore permits simplified multiple hole drilling, while the CAS system accurately measures the depth of each hole created.

The embodiments of the invention described above are intended to be exemplary only. The scope of the invention is therefore intended to be limited solely by the scope of the appended claims.

What is claimed is:

1. A drill guide assembly for a drilling tool having a chuck engaging a bit portion comprising a tip and a length extending from the chuck, said drill guide assembly comprising:
   a first member adapted to abut a workpiece surface and defining a central aperture therethrough adapted to receive the bit portion of the drilling tool;
   a second member adapted be axially displaced with respect to said first member and being axially biased therefrom, and defining a central aperture therethrough adapted to receive the bit portion of the drilling tool; and
   a trackable member, fastened to said second member and comprising a detectable element adapted to be located and tracked in three dimensional space, thereby defining position and movement of said second member and therefore that of the bit portion of the drilling tool.

2. The drill guide assembly as defined in claim 1, wherein said first and second members are elongated and telescope with respect to each other.

3. The drill guide assembly as defined in claim 1, wherein the length of the bit portion of the drilling tool is chosen such that the tip reaches said workpiece surface when said first and second members are fully biasedly extended.

4. The drill guide assembly as defined in claim 2, wherein a distance said elongated second member telescopes with respect to said elongated first member, corresponds to a hole depth created by the bit portion of the drilling tool in a workpiece.

5. The drill guide assembly as defined in claim 1, wherein said detectable element comprises a three point visually located axis.

6. The drill guide assembly as defined in claim 1, wherein said central aperture of said second member is dimensioned to intimately receive said first elongated member.

7. The drill guide assembly as defined in claim 1, wherein said second member is spring loaded from said first member.

8. The drill guide assembly as defined in claim 7, wherein an outer clamp is engaged with said first member, a circumferential flange radially extends from said second member, and said clamp and said flange provide end reaction points for a helical spring providing said spring loaded second member.

9. The drill guide assembly as defined in claim 1, wherein said drill guide assembly comprises a handle element.

10. The drill guide assembly as defined in claim 9, wherein said handle element comprises at least a portion that extends generally radially from said first and second members.

11. The drill guide assembly as defined in claim 9, wherein said handle element is selectively rotatable about said drill guide assembly to maintain said tracking member in detectable contact with a sensor of a computer assisted surgery system.

12. The drill guide assembly as defined in claim 10, wherein said handle element is engaged with said first member.

13. The drill guide assembly as defined in claim 1, wherein a proximal end of said second member comprises a bushing.

14. The drill guide assembly as defined in claim 1, wherein said detectable element comprises optically detectable spheres.

15. The drill guide assembly as defined in claim 14, wherein said optically detectable spheres are removably engaged with said trackable member.

16. A drilling system comprising a drill and a drill guide assembly, the drill having a chuck engaging a bit portion having a tip and extending from the chuck a predetermined length, said drill guide assembly comprising:
   a guide member defining a central aperture therethrough adapted to receive the bit portion of the drilling tool;
   a collar member defining a central aperture therethrough dimensioned to intimately receive said guide member;
   said collar member and said guide member being axially biased, and adapted to telescope with respect to one another;
   one of said guide member and said collar member being adapted to abut a workpiece surface, the other of said guide member and said collar member being adapted to be axially displaced with respect to said one of said guide member and said collar member; and
   a trackable member, fastened to said other of said guide member and said collar member, having detectable element adapted to be located and tracked in three dimensional space, said detectable element defining the position and movement of said other of said guide member and said collar member, and therefore defining the position and movement of the bit portion of the drilling tool.

17. The drilling system as defined in claim 16, wherein the predetermined length of the bit portion of the drilling tool is such that the tip reaches said workpiece surface when said guide and collar members are fully biasedly extended.

18. The drilling system as defined in claim 16, wherein said central aperture of said member is dimensioned to intimately receive said guide member.

19. The drilling system as defined in claim 16, wherein said collar member is spring loaded from said guide member.

20. The drilling system as defined in claim 19, wherein an outer clamp is fastened to said one of said guide member and said collar member, a circumferential flange radially extends from said other of said guide member and said collar member, and said clamp and said flange provide end reaction points for a helical spring providing said spring loaded collar member.

21. The drilling system as defined in claim 16, wherein said drill guide assembly comprises a handle element.

22. The drilling system as defined in claim 21, wherein said handle element comprises at least a portion that extends generally radially from said collar and guide members.

23. The drilling system as defined in claim 16, wherein said handle element is selectively rotatable about said drill guide assembly to maintain said tracking member in detectable contact with a sensor of a computer assisted surgery system.

24. The drilling system as defined in claim 21, wherein said handle element is engaged with said one of said guide member and said collar member.

25. The drilling system as defined in claim 16, wherein a proximal end of said collar member comprises a bushing.

26. The drilling system as defined in claim 16, wherein said detectable element comprises optically detectable spheres.

27. The drilling system as defined in claim 26, wherein said optically detectable spheres are removably engaged with said trackable member.

* * * * *